United States Patent
Wetzel et al.

(10) Patent No.: US 6,977,238 B1
(45) Date of Patent: Dec. 20, 2005

(54) METHOD FOR MAKING STABLE AQUEOUS FOAMING SURFACTANT

(75) Inventors: Thierry Wetzel, Brussels (BE); Marie Claire Leona Hilda Taelman, Wortegem-Petegem (BE)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 08/930,702

(22) PCT Filed: Mar. 19, 1996

(86) PCT No.: PCT/GB96/00632

§ 371 (c)(1),
(2), (4) Date: Feb. 13, 1998

(87) PCT Pub. No.: WO96/31187

PCT Pub. Date: Oct. 10, 1996

(30) Foreign Application Priority Data

| Apr. 4, 1995 | (GB) | ............................................. 9506927 |
| Feb. 27, 1996 | (GB) | ............................................. 9604018 |

(51) Int. Cl.⁷ ............................................. A61K 7/00
(52) U.S. Cl. .................... 510/130; 510/156; 424/70.19; 424/70.1; 424/401; 514/945
(58) Field of Search ................................. 510/130, 156; 424/70.1, 70.19, 401, 78.02; 514/945

(56) References Cited

U.S. PATENT DOCUMENTS

| 4,198,311 | A | * | 4/1980 | France et al. |
| 5,248,495 | A | | 9/1993 | Patterson et al. |
| 5,543,074 | A | * | 8/1996 | Hague et al. ................ 510/122 |

FOREIGN PATENT DOCUMENTS

| EP | 0485212 | 5/1992 |
| WO | 94/17166 | 8/1994 |

* cited by examiner

Primary Examiner—Necholus Ogden
(74) Attorney, Agent, or Firm—Mayer, Brown, Rowe & Maw, LLP

(57) ABSTRACT

Stable aqueous dispersions of foaming surfactants are prepared by starting with a pre-formed substantially uniform surfactant composition which contains one or more foaming surfactants, and one or more fatty amphiphiles. The dispersion contains from 5 to 50 wt % of the surfactant composition and from 50 to 95 wt % water. A hydrocolloid is also preferably included in the dispersion. Emollients are also conveniently included in the aqueous dispersion.

8 Claims, No Drawings

METHOD FOR MAKING STABLE AQUEOUS FOAMING SURFACTANT

This application is a 371 of PCT/GB96/00632, filed Mar. 19, 1996. This invention relates to surfactant compositions and in particular to surfactant compositions that contain foaming surfactants and emollient materials and to methods of making such compositions.

Surfactant compositions containing emollient materials are known, particularly in the form of personal care products notably shower gels, creaming foam bath products, shampoos, facial wash and body scrub products. Commercially these products, particularly the shower gel products, are often sold as so-called "2 in 1" products. Typically these materials are aqueous emulsions of emollient materials, usually an emollient oil, including one or more surfactant materials dispersed usually in the aqueous phase, but sometimes also in the oil phase. The intent is that the surfactant material(s) act as cleaning agents, and are usually chosen to produce a foaming creamy lather on dispersion into water in the skin or hair, particularly in use as shower gels, foaming cream bath products or shampoos, and the emollient acts to prevent evaporation of skin moisture by restoring the protective layer lost by removal of skin lipids by the detergent in the cleansing product, thus making the later use of a moisturising cream or milk unnecessary. Emollients, particularly emollient oils tend to be incompatible with the foaming surfactants, such as fatty alkyl ether sulphates and betaine surfactants that are commonly used in these products, indeed some emollient oils can act as antifoams. Products that show foaming surfactancy, stability in storage and emollient properties usually have to be carefully formulated and the choice and proportions of the constituents is usually critical. The order of process steps is also often critical to success, particularly as the use of high energy mixing in the presence of highly foaming surfactants is likely to give uncontrolled foaming during processing. The specific formulations and processes that are required to achieve a stable product make for difficulty for manufacturers in developing products as the process needs to be developed separately for each product and makes manufacturing and inventory logistics complicated as there may be little in common in formulation between products that are otherwise ostensibly similar.

The present invention is based on our discovery that the manufacture of such products can be greatly simplified by the use of a pre-formed surfactant dispersion containing surfactant materials, especially mild surfactant materials, fatty amphiphile and optionally but very desirably hydrocolloid either as a dispersion in water, or and very desirably as a solid mix which can then be dispersed in water. When the pre-formed surfactant dispersion is a solid mix, an emollient can be included in the composition either by addition to the aqueous phase before addition of the (solid) surfactant dispersion or added to the water (or the water added to it) at the same time or after addition of the surfactant dispersion. This provides great flexibility in manufacturing processes. We believe that some of the products that can be made by our new simplified process are in themselves new, although products can be made that have compositions that are the same as or similar to known 2 in 1 products that are commercially available.

The present invention accordingly provides, in a first product aspect, a stable aqueous foaming surfactant dispersion which comprises:

from 5 to 50 weight % of a surfactant composition comprising at least one foaming surfactant, at least one fatty amphiphile and optionally, but very desirably, at least one hydrocolloid; and
from 50 to 95 weight % of water.

The invention also includes, in a second product aspect, a stable aqueous foaming dispersion of a surfactant comprising at least one foaming surfactant, particularly including at least one anionic surfactant, at least one fatty amphiphile and optionally, but very desirably, at least one hydrocolloid, the dispersion also including emulsified therein at least one emollient.

As well as the products the invention includes methods of making surfactant compositions containing emollients and accordingly the present invention provides in a first process aspect a method of making a stable aqueous foaming surfactant dispersion, which comprises dispersing in water, a preformed substantially uniform solid surfactant composition comprising at least one foaming surfactant, at least one fatty amphiphile and optionally, but very desirably, at least one hydrocolloid; in weight proportions to give a composition containing from 5 to 50 weight % of the surfactant composition and from 50 to 95 weight % of water.

The invention further includes in a second process aspect, a method of making a stable aqueous foaming surfactant dispersion, which comprises forming an aqueous dispersion of a surfactant composition comprising at least one foaming surfactant, at least one fatty amphiphile and optionally, but very desirably, at least one hydrocolloid; and subsequently dispersing therein at least one emollient.

The invention specifically includes three variations on the basic process using a pre-formed solid surfactant blend of surfactant, fatty amphiphile and hydrocolloid:

(i) A method of making a stable aqueous foaming surfactant dispersion, which comprises mixing from 5 to 50 parts by weight of a pre-formed solid surfactant blend, containing surfactant, fatty amphiphile and hydrocolloid, with the emollient, and optionally other components, adding from 50 to 95 parts by weight of water at a temperature of from 60 to 90° C., particularly 70 to 90° C., homogenising the mixture to disperse the surfactant blend and emulsify the emollient.

(ii) A method of making a stable aqueous foaming surfactant dispersion, which comprises dispersing from 5 to 50 parts by weight of a pre-formed solid surfactant blend, containing surfactant, fatty amphiphile and hydrocolloid, in from 50 to 95 parts by weight of water at a temperature of from 60 to 90° C., particularly 70 to 90° C., homogenising the mixture to disperse the surfactant blend and subsequently adding an emollient to the dispersion.

(iii) A method of making a stable aqueous foaming surfactant dispersion, which comprises adding from 50 to 95 parts by weight of water at a temperature of from 60 to 90° C., particularly 70 to 90° C. to from 5 to 50 parts by weight of a pre-formed solid surfactant blend, containing surfactant, fatty amphiphile and hydrocolloid, homogenising the mixture to disperse the surfactant blend and subsequently adding an emollient to the dispersion.

As is indicated above, the products of and made by the method of the invention are particularly intended for use as personal care products, especially as shampoos and shower gels and the invention specifically includes products of the invention in the form of a shampoo or a shower gel and the use of products of or made by the method of the invention as shampoos or shower gels.

The foaming surfactant can be or include an anionic, non-ionic, or amphoteric surfactant materials. Suitable anionic types of surfactant include alkyl sulphates, such as lauryl, oleyl and stearyl sulphates, alkyl sulphonates, alkyl ether sulphates, alkyl glycerol ether sulphonates, alkyl phosphate esters, ethoxylated alkyl phosphate esters, sarcosinates, taurate derivatives, alkyl sulphoacetates, hydroxyalkyl sulphonate esters, such as isethionate esters, particularly of fatty carboxylic acids, for example cocoyl isethionic acid, lauryl isethionic acid and stearyl isethionic acid (usually used as the sodium salt), alkyl sulphosuccinates, such as sodium and/or potassium lauryl, oleyl and stearyl sulphosuccinates, alkyl sulphosuccinamates, and acyl glutamates. Such anionic surfactants are usually used as metal, usually alkali metal especially sodium or potassium, ammonium or ethanolamine salts. The alkyl chains in such surfactants are typically $C_{12\ to\ 20}$, more usually $C_{14\ to\ 18}$ chains. Suitable non-ionic types of surfactant include alkyl polysaccharides especially alkyl polyglucosides, sorbitan ester alkoxylates, and glucamide surfactants. Suitable amphoteric surfactants include betaine derivatives, imidazoline derivatives, and fatty amphoacetates, particularly coco-amphoacetates. The surfactants may also include soaps, particularly fatty acid alkali metal soaps such as sodium and/or potassium stearate.

As used in personal care products, it may be desirable to include mild surfactants. Foaming anionic surfactants are usually used as alkali metal salts of acidic groups and if the acid group is a relatively weak acid the salt will give an alkaline mixture in water that can be aggressive to the human skin. To reduce the aggression of the surfactant, it is desirable to use anionic surfactants where the hydrophile is the anionic residue of a relatively strong acid group, usually a sulphate or more usually a sulphonate group. Typical examples of such surfactants include esters of carboxylic acids including fatty, particularly $C_{8\ to\ 20}$ alkyl, substituents with hydroxyalkylsulphonic acids such as isethionic acid (2-hydroxyethane sulphonic acid; $HO.CH_2.CH_2.SO_3H$), as salts, usually alkali metal salts, particularly sodium salts of $C_{12\ to\ 20}$ carboxylic isethionates, especially sodium cocoylisethionate. Combinations of isethionate surfactants and sulphosuccinate surfactants, for example approximately equal proportions of sodium cocoyl isethionate and sodium sulphosuccinate, give particularly good results. Such mild surfactants can be used alone or in combination with other (more harsh) surfactants, but such mixtures will have intermediate mildness properties.

The use of such mild surfactants is an important feature of the invention such that it forms a specific part of the invention so that the first product aspect of the invention accordingly includes: a stable aqueous foaming surfactant dispersion which comprises:

from 5 to 50 weight % of a surfactant composition comprising at least one fatty isethionate foaming surfactant, optionally but desirably at least one sulphosuccinate salt, at least one fatty amphiphile and optionally, but very desirably, at least one hydrocolloid; and from 50 to 95 weight % of water;

and the second product aspect of the invention accordingly includes a stable aqueous foaming dispersion of a surfactant comprising at least one fatty isethionate foaming surfactant, optionally but desirably at least one sulphosuccinate salt, at least one fatty amphiphile and optionally, but very desirably, at least one hydrocolloid, the dispersion also including emulsified therein at least one emollient oil.

In these mild surfactant based products, the surfactant is desirably mainly or predominantly a mild surfactant, in particular, at least 50%, desirably at least 75% and especially at least 90%, by weight of the surfactant is a mild surfactant, particularly an alkyl sulphonate and/or a fatty isethionate. This again forms a specific aspect of both the first and second product aspects of the invention.

The term "fatty amphiphile" refers to compounds which are normally insoluble in water and include a fatty chain, usually an alkyl chain, and a polar hydrophilic group. The polar hydrophilic group is not such as to give the compound water solubility, although it will generally assist in making the compound dispersible in water, and the compound is not sufficiently hydrophilic as to act as an effective surfactant in the system; in other words any contribution to surfactancy is small in comparison to the effect of the foaming surfactant. Suitable materials include fatty alcohols, particularly $C_{8\ to\ 24}$, especially $C_{14\ to\ 20}$ fatty alcohols such as stearyl alcohol, for example as tallow alcohol and also as commercially available under the technical descriptions cetostearyl alcohol or cetearyl alcohol; fatty acids, particularly $C_{8\ to\ 24}$, especially $C_{14\ to\ 20}$ fatty acids such as stearic acid; glyceride fatty esters, particularly mono-, di- and tri-glycerides of $C_{8\ to\ 24}$, especially $C_{14\ to\ 20}$ fatty acids such as glyceryl mono- and di-stearate, laurate, palmitate and similar materials; and esters of fatty acids, particularly $C_{8\ to\ 24}$, especially $C_{14\ to\ 20}$ fatly acids such as lauric and stearic acid, with polyhydric alcohols such as sorbitan, such as sorbitan laurate. As with fatty alcohols, other fatty amphiphiles (and, of course other components of the system) are commonly available and will be used as mixtures of materials e.g. from a natural source, a distillation cut during manufacture or deliberately blended to give a mixture. Although the role of the fatty amphiphile is not fully understood, it appears to contribute to structure in the aqueous phase of the system (even though itself it may not be in solution in the water) and thus to enhance the dispersion of the components of the system.

The hydrocolloid is a hydrophilic material that can be colloidally dispersed in the aqueous system. Typically such materials can be organic or inorganic materials. Organic hydrocolloids are usually polymers of monomers including hydrophilic groups and suitable examples include starch e.g. corn starch and wheat starch, modified starches e.g. partly etherified starches, or dextrins, guar, modified guar and similar polysaccharides, modified celluloses such as carboxyalkyl, especially carboxymethyl, celluloses, xanthan gums, hydrophilic carbomer polymers polyacrylamides, polyvinyl alcohol, polyvinylpyrrolidone, polyacrylates and very high molecular weight polyethylene glycol. Inorganic hydrocolloids are usually oxides with hydrophilic surfaces and suitable examples include water dispersible bentonite clays and aluminium silicates. The hydrocolloid seems to act as an aqueous phase viscosifier, rheology modifier and hydrophilic structurant. We have found that the hydrocolloid can give a marked improvement in the stability of the dispersed products, especially on extended storage or storage at relatively high temperatures (as accelerated storage tests—but akin to normal user storage in bathrooms). In compositions containing hydrocolloids, we have had no difficulty in achieving compositions stable to cycle testing for 3 months in the cycle: 50° C./40° C./ambient temperature/−5° C. and for 1 month in the cycle −5° C./40° C. (12 hours/12 hours). In referring to stable compositions herein, we refer to compositions that meet these stability testing standards.

The emollient is included in the formulation to improve the skin feel and moisturising or conditioning properties of the overall formulation. The emollient can and usually will be an oily material which is liquid at ambient temperature. Alternatively it can be solid at ambient temperature, in which case in bulk it will usually be a waxy solid, provided it is liquid at an elevated temperature at which it can be included in and emulsified in the composition. As is described below manufacture of the composition usually uses temperatures up to 100° C. so such solid emollients will have melting temperatures of less than 100° C. and usually less than 70° C. Suitable normally liquid emollient oils include non-polar oils, for example mineral or paraffin, especially isoparaffin, oils, such as that sold by ICI Surfactants as Arlamol HD, or polar oils, for example vegetable glyceride oils, animal glyceride oils, such as that sold by ICI Surfactants as Arlamol M812 (caprylic/capric triglyceride), synthetic oils, for example synthetic ester oils, such as those sold by ICI Surfactants as Arlamol IPM and Arlamol DOA, or silicone oils, such as dimethicione oil, or silicones having polyoxyalkylene side chains to improve their hydrophilicity. Suitable emollient materials that can be solid at ambient temperature but liquid at temperatures typically used to make the compositions of this invention include jojoba wax, tallow and coconut wax/oil. Mixtures of emollients can and often will be used and in some cases solid emollients may dissolve wholly or partly in liquid emollients. Where the emollient is a solid at ambient temperature, the resulting dispersion may technically not be an emulsion (although in most cases the precise phase of the oily disperse phase cannot readily be determined) but such dispersions behave as if they were true emulsions and the term emulsion is used herein to include such compositions.

From the discussion above, it can be seen that some materials can fall within the definition of both emollient oil and the fatty amphiphile. We believe that it is for this reason that compositions containing fatty amphiphile can give creamy dispersions in water, that foam readily and have good skin feel and seem to be emollient, even when no emollient oil is specifically added to the composition. Fatty alcohols, such as stearyl alcohol, and acids and mono- and di-glycerides are fatty amphiphiles that can also act as emollients.

In the formulations of and made by the methods of the invention, the intent is to form creamy emulsions having good skin feel. We have found that such emulsions typically have swollen surfactant bilayers which wholly or partly enclose the particles or droplets of the disperse phase. This sort of morphology seems to be found in emulsions that give a creamy skin feel and are stable. The presence of such bilayers has been shown to improve moisturising and skin conditioning properties.

The formulations for the invention can have visocsities appropriate for personal care compositions ranging from milks and lotions to creams. Thus the dispersions of the surfactant, fatty amphiphile and hydrocolloid (when present) in water typically have viscosities of the following order for dispersions in water at the stated percentages:

| Concentration (% by wt.) | 25 | 30 | 35 | 40 |
|---|---|---|---|---|
| Viscosity (Pa.s) | 2 | 45 | 60 | 500 |

The major components of the compositions of and made by the methods of the invention are typically present in the following proportions (parts by weight):

| material | broad range | usual range | typical values |
|---|---|---|---|
| surfactant | 10–60 | 30–55 | about 50 |
| fatty amphiphile | 5–30 | 10–25 | about 15 |
| hydrophillic colloid | 0–35 | 15–30 | about 25 |
| emollient oil | 0–30 | 10–25 | about 20 |

In formulations of and made by the invention, the proportion of water is in the range 50 to 95% based on the combined weights of water, surfactant, fatty amphiphile and hydrocolloid (when present). Within this range, the amount of water is typically from 55 to 95, more usually 60 to 80% by weight with corresponding proportions of combined surfactant, fatty amphiphile and hydrocolloid (when present).

Other materials that can be included in the compositions include the materials set out below:

Lubricants and/or humectants particularly polyols such as glycerol, sorbitol, propylene glycol, butylene glycol, polyoxyethylene sorbitol, polyoxyethylene glycerol esters, polyethylene glycol (PEG) (particularly liquid PEG's up to PEG 400) and polyoxyethylene methyl glucoside. Such materials act in the final compositions as humectants and antifreeze components and can improve the skin feel of the products. They can also give a process advantage as they can act as lubricants in solid surfactant compositions which can be used as intermediate materials in the process of this invention. This can make manufacture of the solid surfactant composition easier and make the solid formulation more uniform.

Disperse phase structurants, such as water dispersible waxes for example vegetable and animal derived waxes, such as beeswax, synthetic waxes and mineral or petroleum waxes. The structurant will typically be used in an amount of about 1 to about 10%, more usually from about 2 to about 8%, particularly about 2 to about 6% of a preformed surfactant blend, and typically in an amount of about 0.2 to 4%, more usually about 0.5 to about 2%, for example about 0.5 to about 1% by weight, of an aqueous dispersion of the invention.

Fillers, pigments, dyes and optical brighteners, such as titanium dioxide; polyquaternary ammonium compounds as conditioning agents; perfumes, fragrances and/or, essential oils; water and/or oil soluble vitamins or derivatives or precursors; antioxidants and/or preservatives (typically in an amount of up to ca 1%); pearlescing agents; peeling and/or scrub agents; plant extracts, particularly water soluble plant extracts; hydroxy-, particularly alpha-hydroxy, and/or polyunsaturated acids; phospholipids; proteins and/or amino acids and/or derivatives; electrolytes; NMF (natural moisturising factor); foam boosters and/or stabilisers e.g. mono- and/or di-ethanolamides and/or amine oxides; and sucrose ester derivatives.

The products of this invention can be made by a variety of methods. Generally the methods involve dispersion of the surfactant in water which is typically at elevated temperature, usually from of from 60 to 100° C., particularly 70 to 90° C., more usually from 75 to 95° C. We have found that there can be considerable flexibility in the order of addition of the various components, especially where the surfactant, fatty amphiphile and, where used, hydrocolloid are in the form of a pre-formed solid surfactant blend, which is typically used in the form of flakes. For convenience, oily components of the formulation e.g. the emollient and other oil soluble materials are pre-mixed to form an oily component, similarly the water soluble materials components are pre-mixed to form a water soluble component. Generally perfumes are kept separate from these components as they are added separately to the product at relatively low temperatures, typically below 40° C. e.g. about 35° C., to avoid undue loss by volatilisation.

In a first such method, the surfactant blend, the oily component and the water soluble component are mixed and then the water is added to them, typically at a temperature of from 60 to 90° C., particularly 70 to 90° C., e.g. about 80° C., and the mixture stirred at the elevated temperature, to make it uniform. For this, moderate stirring e.g. using a paddle stirrer at 250 to 500 rpm (ca 4 to 8.5 Hz) for typically 10 to 15 minutes, seems satisfactory. The mixture is then stirred more vigorously at the elevated temperature to emulsify the oily component. For this stirring using a rotor-stator mixer (on a laboratory scale an Ultra Turrax stirrer has proved satisfactory) at from 6000 to 12000 rpm (100 to 200 Hz) e.g. ca. 9000 rpm (150 Hz), for from 30 seconds to 3 minutes, typically about 1 minute, has proved sufficient. Subsequently, the mixture is cooled to ambient temperature, usually under gentle stirring, and the perfume, if any, added when the temperature is about 35° C.

In a second such method, hot water (typically at a temperature of from 60 to 100° C., particularly from 75 to 95° C. e.g. at about 90° C. is added to the surfactant blend, the mixture is stirred as described above to make it uniform and then more vigorously to homogenise it. The oily component and the water soluble component are added after homogenisation, during subsequent cooling under gentle stirring to ambient temperature (adding any perfume at about 35° C.), or after the mix has cooled to ambient temperature provided that the oily components are liquid at the temperature they are added to the mixture. Desirably, the water soluble components are also liquid at the addition temperature (or are added as an aqueous solution). It seems that even gentle stirring of the oily component into the homogenised surfactant blend in water can give a well dispersed emulsion of the oily component in the aqueous mix.

In a third such method, the surfactant blend is added to hot water, typically at a temperature of from 60 to 90° C., particularly 70 to 90° C., e.g. about 100° C., and the mixture is stirred as described above to make it uniform and then more vigorously to homogenise it. The oily component and the water soluble component are added after homogenisation, during subsequent cooling under gentle stirring to ambient temperature (adding any perfume at about 35° C.), or after the mix has cooled to ambient temperature the oily components are liquid when added at the temperature they are added to the mixture. Desirably, the water soluble components are also liquid at the addition temperature (or are added as an aqueous solution). It seems that even gentle stirring of the oily component into the homogenised surfactant blend in water can give a well dispersed emulsion of the oily component in the aqueous mix.

Uses for the compositions of and made by the method of the invention include: 2 in 1 shower formulations, in effect combining a shower gel type surfactant formulation and a body milk or cream; foaming cream bath formulations; cream shampoos; make-up remover liquid or cream, liquid emulsion for impregnating make-up remover tissues; creamy hand soap formulations; facial cleanser formulations; foaming face cream formulations; scrub/peeling cream, especially for use on the face. In such end uses the compositions used according to this invention will usually and advantageously be based on mild surfactants as is described above and the use of mild surfactants in these end uses and in formulations for such end uses forms a specific subsidiary aspect of this invention.

The following Examples illustrate the invention. All parts and percentages are by weight unless otherwise stated.

Materials

Surfactant Blends (SB)

these are pre-formed flaked solid blends containing surfactant, fatty amphiphile and hydrocolloid in the amounts indicated for the particular blends given below. The particular blend used in the Examples are abbreviated SBA, SBB and SBC.

| Material | parts by weight |
|---|---|
| SBA a surfactant blend having the following composition by weight: | |
| sodium cocoyl isethionate | 5 |
| sodium lauryl sulphosuccinate | 5 |
| betaine surfactant | 0.3 |
| stearyl alcohol | 3 |
| structurant wax | 0.5 |
| corn starch | 5 |
| humectant, pigment etc. | 1.5 |
| SBB a surfactant blend having the following composition by weight: | |
| sodium cocoyl isethionate | 6.5 |
| sodium lauryl sulphosuccinate | 6 |
| betaine surfactant | 0.3 |
| tallow alcohol | 3.7 |
| structurant wax | 1.2 |
| wheat starch | 5 |
| humectant etc. | 2 |
| SBC a surfactant blend having the following composition by weight: | |
| sodium cocoyl isethionate | 6.5 |
| sodium lauryl sulphosuccinate | 6 |
| betaine surfactant | 0.3 |
| tallow alcohol | 3.7 |
| structurant wax | 1.2 |
| starch | 5 |
| humectant etc. | 2 |

| | |
|---|---|
| Arlamol 812 | Caprylic/capric triglyceride emollient ex ICI Surfactants |
| Arlamol HE | PEG-7 glyceryl cocoate ex ICI Surfactants |
| Arlamol HD | Isoparaffin (isohexadecene) emollient ex ICI Surfactants |
| Arlamol POA8 | Polydecene emollient ex ICI Surfactants |
| Arlamol DOA | Dioctyladipate emollient ex ICI Surfactants |
| Arlamol E | Polypropylene glycol stearyl ether emollient ex ICI Surfactants |
| Arlamol F04/G50 | Perfluoropolymethylisopropylether in glycerine ex ICI Surfactants |
| Germaben II | Preservative ex Sutton Laboratories |
| Florabeads | Jojoba Wax Beads ex Floratech (emollient solid at ambient temperature) |
| Florasun 90 | sunflower oil ex Floratech |
| Keltrol F | Xanthan Gum ex Kelco |
| Polymer JR125 | Polyquaternary ammonium polymer as conditioner, ex Union Carbide |
| Silicone Oil | Dimethicone a silicone oil having a stated viscosity of 100 mPa.s. |
| Brij 72 | stearyl alcohol 2EO derivative ex ICI Surfactants |
| Brij 721 | stearyl alcohol 21EO derivative ex ICI Surfactants |

-continued

| | |
|---|---|
| Laurex CS | fatty alcohol (mainly stearyl alcohol) ex Marchon |
| Tensiomild HM 935 | ethoxylated lauryl alcohol sulphosuccinate ester disodium salt ex Hickson Manro |
| Tegobetain L7 | cocamidopropylbetaine ex Goldschmidt |
| Atlas G-1823 | solublised PEG 6000 distearate ex ICI Surfactants |
| Atlas G-2330 | sorbitol 30EO derivative ex ICI Surfactants |
| Arlatone 2121 | a blend of sorbitan stearate and sucrose cocoate ex ICI Surfactants |
| Arlatone 1489 | decyl glucoside and sodium cocoylisethionate in water ex ICI Surfactants |
| Clearam CH 40 | esterified waxy maize starch ex Roquette |
| Glucidex V17 | sodium carboxymethyl starch ex Roquette |
| Guar C261 N | Cosmedia Guar C261 N - Guar hydroxypropyltrimonium chloride ex Henkel |

Test Methods

Viscosity measurements on formulations were made using a Brookfield LVT viscometer at 25° C., 6 rpm (0.1 Hz) and a spindle (from types A to F); values are quoted in Pa.s.

Manufacturing Examples

The manufacturing methods described below all use four components:
1 the surfactant blend SBA as described above (SB)
2 the oil soluble additives (OSA)—the emollient and any other oil soluble materials
3 the water soluble additives (WSA)—such as additional hydrocolloid e.g. xanthan
4 water (distilled water was used in the Examples below)

The amounts used vary depending on the product being produced and are indicated below in the Formulation Examples. The methods use a mixing vessel for the main method steps.

Manufacturing Methods

Method 1: (400 g to 2 kg batch scale)
1 the water is heated to 90° C.;
2 the surfactant blend, the oil soluble additives and the water soluble additives are weighed into the mixing vessel;
3 The water is added to the mixture in the mixing vessel under moderate stirring, about 250 to 500 rpm (ca. 40 to 80 Hz) keeping the temperature at about 80° C. The stirring is continued for 10 to 15 min. until a uniform dispersion is obtained;
4 The mixture is homogenised at 80° C. by stirring with a rotor/stator type mixer (Ultra-Turrax) at about 9000 rpm (150 Hz) for about 1 minute;
5 The mixture is cooled to ambient temperature under gentle stirring;
6 during cooling the perfume is added to the emulsion when the temperature is about 35° C.

In a minor variation of this method, the homogenisation step is carried out immediately before cooling.

Method 2: (400 g to 2 kg batch scale)
1 Hot water at 90° C. is added to the surfactant blend in the mixing vessel
2 the mixture is stirred (at about 250 to 500 rpm) keeping the temperature at about 80° C. for 10 to 15 min. until a uniform dispersion is obtained;
3 The mixture is homogenised at 80° C. by stirring with a rotor/stator type mixer (Ultra-Turrax) at about 9000 rpm for about 1 minute;
5 The mixture is cooled to ambient temperature under gentle stirring;
6 before during or after cooling the oil soluble additives and the water soluble additives are added as liquids to the mixture (under gentle stirring);
7 during cooling the perfume is added to the emulsion when the temperature is about 35° C.

Method 3: (400 g to 2 kg batch scale)
1 The surfactant blend (as flakes) is added to hot water at 80° C. in the mixing vessel under moderate stirring (at about 250 to 500 rpm) keeping the temperature at about 80° C. for 10 to 15 min. until a uniform dispersion is obtained:
2 The mixture is homogenised at 80° C. by stirring with a rotor/stator type mixer (Ultra-Turrax) at about 9000 rpm for about 1 minute;
3 The mixture is cooled to ambient temperature under gentle stirring;
4 before during or after cooling the oil soluble additives and the water soluble additives are added as liquids to the mixture (under gentle stirring);
5 during cooling the perfume is added to the emulsion when the temperature is about 35° C.

FORMULATION EXAMPLES (FE1 to FE7)

These Examples give the percentages (w/w) of materials used to make the products referred to. Any the methods described above can be used for any of the Formulation Examples FE1 to 7.

FORMULATION EXAMPLE 1

"2-in-1" shower gel + body milk

| | Material | % (w/w) |
|---|---|---|
| SB | SBA | 30.0 |
| OSA | Arlamol M812 | 5.0 |
| | Arlamol HE | 3.0 |
| WSA | Germaben II | 1.0 |
| Water | | to 100 |

This product has a viscosity of 30 Pa.s

FORMULATION EXAMPLE 2

"2-in-1" shower gel + body milk

| | Material | % (w/w) |
|---|---|---|
| SB | SBA | 35.0 |
| OSA | Silicone oil | 5.0 |
| WSA | Germaben II | 1.0 |
| Water | | to 100 |

This product has a viscosity of 60 Pa.s

FORMULATION EXAMPLE 3

Foaming cream bath

| | Material | % (w/w) |
|---|---|---|
| SB | SBA | 25.0 |
| OSA | Arlamol HE | 5.0 |
| WSA | Germaben II | 1.0 |
| Water | | to 100 |

This product has a viscosity of 20 Pa.s

FORMULATION EXAMPLE 4

Foaming scrub cream for face and body

| | Material | % (w/w) |
|---|---|---|
| SB | SBA | 35.0 |
| OSA | Florabeads | 5.0 |
| WSA | Germaben II | 1.0 |
| Water | | to 100 |

This product has a viscosity of 60 Pa.s

FORMULATION EXAMPLE 5

Liquid make-up remover

| | Material | % (w/w) |
|---|---|---|
| SB | SBA | 20.0 |
| OSA | Arlamol HD | 5.0 |
| WSA | Keltrol F | 0.3 |
| | Germaben II | 1.0 |
| Water | | to 100 |

This product has a viscosity of 5 Pa.s

FORMULATION EXAMPLE 6

Foaming face cream

| | Material | % (w/w) |
|---|---|---|
| SB | SBA | 35.0 |
| OSA | Arlamol HD | 2.0 |
| WSA | Germaben II | 1.0 |
| Water | | to 100 |

This product has a viscosity of 40 Pa.s

FORMULATION EXAMPLE 7

Conditioning cream shampoo

| | Material | % (w/w) |
|---|---|---|
| SB | SBA | 30.0 |
| OSA | Polymer JR125 | 0.1 |
| WSA | Germaben II | 1.0 |
| Water | | to 100 |

This product has a viscosity of 35 Pa.s

FORMULATION EXAMPLES 8 to 15

The formulations of Formulation Examples FE8 to FE15 were made up using, in three samples of each Example, a at 25%, b at 33% and c at 38% of SBB, including 0.2% Keltrol and 3% of various Emolients/Oils (with water to 100%) by dispersing the SBB in the water at about 80° C. under stirring and then adding Keltrol and then the oil to give the formulations summarised in Table 1 below. Table 1 includes the viscosity of the oils used (OV) measured at ambient temperature [Brookfield viscometer, spindle 1 at speed 12–60 s for FE's 8 to 14 and 6–60 s for FE 15, values in mPa.s] and oil/water interfacial tensions (IT) [measured by a Krüss tensiometer or from the supplier's literature, values in $mN.m^{-1}$]. The viscosity of each of the three formulations of FE's 8 to 15 was measured 1 day and 1 month after the formulation was made up. The storage stability of the formulations was also measured after storage at ambient temperature (Amb), 5° C., 40° C. and 50° C. Quantitative viscosity and storage stability testing data are included in Table 1 below.

FORMULATION EXAMPLES 16 and 17

The surfactant blend can be used flexibly to make a variety of different end products. To illustrate this two products were made by mixing 10% of one of two oil-in-water emulsion creams into an aqueous mix of SBB (35%), preservative (as required, typically ca 1%) and water (to 100% overall). The products were made by heating the water to 80° C. adding the SBB (as flakes) with gradual stirring at 75 to 80° until the surfactant blend is homogeneously dispersed, the dispersion was cooled under gentle stirring to about 35° C. and the oil-in-water emulsion cream was added.

The oil-in-water emulsion creams were, for FE16, an 'oleosome' cream of the composition:

| Material | Parts by wt |
|---|---|
| an oil phase made up of: | |
| Brij 72 | 3.0 |
| Brij 721 | 2.0 |
| Arlamol E | 4.0 |
| Arlamol HD | 5.0 |
| Laurex CS | 1.0 |
| Stearic Acid | 1.5 |
| Silicone Oil | 1.0 |
| dispersed in an aqueous phase of: | |
| propylene glycol | 4.0 |
| preservative (as required) | ca 1 |
| water | to 100 |
| also including | |
| perfume (Kalica 74519 ex Firmenich) | 0.2 | and, for FE17, a 'hydrosome' cream of the composition

| Material | Parts by wt |
|---|---|
| an oil phase made up of: | |
| Arlamol HD | 10.0 |
| Arlamol M812 | 4.0 |
| Avocado Oil | 2.0 |
| Florasun 90 | 2.0 |

-continued

| Material | Parts by wt |
|---|---|
| α-tocopheryl acetate | 1.0 |
| behenyl alcohol | 2.0 |
| antioxidant blend | 0.1 |
| dispersed in an aqueous phase of: | |
| Arlatone 2121 | 5.5 |
| glycerol | 4.0 |
| preservative (as required) | ca 1 |
| water | to 100 |
| also including | |
| xanthan gum | 0.2 |
| perfume (Bouquet Toujours 916.488 ex Fritzche Dodge and Olcott GmbH) | 0.2 |

FORMULATION EXAMPLES 19 and 20

These Examples illustrate the addition of a surfactant blend (SBB) as used in the present invention to formulated products to act as an opacifier, provide additional emolliency, improve compatibility with oil in the formulation and/or act as a mildness agent.

FE19 (a and b)—Mild Facial Wash 90 or 95 parts by weight of an existing formulation for a mild facial wash having the following composition:

| Material | parts by weight |
|---|---|
| Tensiomild HM 935 | 20.0 |
| Tegobetain L7 | 10.0 |
| Arlatone 1489 | 10.0 |
| sodium chloride | 0.1 |
| Atlas G-1823 | 3.5 |
| preservative (as required) | ca 1 |
| water to | 100 | was heated to about 75° C., 10 or 5 parts of surfactant blend SBB was dispersed in the formulation with gradual stirring and the product cooled to ambient temperature. The final formulation containing 5% SBB (FE 19a) has a viscosity of 25 Pa.s after 1 month (spindle E) and the final formulation containing 10% SBB (FE 19b) has a viscosity of 80 Pa.s after 1 month (spindle F). This laboratory scale preparation was repeated in a 5 kg scale pilot plant run with similar successful results.

FE20—Mild and moisturising cream shower formulation—A formulation having the composition:

| | Material | parts by weight |
|---|---|---|
| A | Florasun 90 | 4.0 |
| | Atlas G-2330 | 2.0 |
| | SBB | 10.0 |
| | Water (overall) to | 100 |
| B | Arlatone 1489 | 10.0 |
| C | urea | 1.0 |
| | Alpantha | 0.5 |
| D | preservative (as required) | ca 1 |
| | perfume (Belle Vue ex Firmenich) | 0.3 |
| E | Atlas G-1823 | 6.0 | was made up by heating the phase A components to 80° C. under gentle stirring until the mix was homogeneously dispersed, adding phase B with gentle stirring, cool under stirring, dissolving the phase C components in water and adding the perfume and preservative to the dispersion at about 35° C. under gentle stirring, and finally adding the Atlas G-1823 under stirring. The final product has a viscosity after one month of about 20 Pa.s (spindle E). In this example, the SBB surfactant blend acts to compatibilise the surfactant and oil and microscopic examination of the product shows the oil dispersed as fine droplets in the surfactant blend.

FORMULATION EXAMPLES 21 to 24

These formulations are further Examples of surfactant formulations including surfactant blends as used in the invention.

FE21—2 in 1 Facial cleansing milk—A formulation having the composition:

| | Material | parts by weight |
|---|---|---|
| A | Keltnol F | 0.2 |
| | Water (overall) to | 100 |
| B | SBB | 25.0 |
| C | preservative (as required) | ca 1 |
| | Arlamol F04/G50 | 0.5 | was made up by heating the water to about 80° C., dispersing the xanthan in the water under gentle stirring, adding the SBB under gentle stirring and maintaining the temperature at about 75 to 80° C. until the mixture was homogeneously dispersed, adding the preservative and Arlamol emollient under gentle stirring and then cooling to ambient temperature under gentle stirring. The final product has a viscosity after one month of about 20 Pa.s (spindle E).

FE22—2 in 1 Shower cream—A formulation having the composition:

| | Material | parts by weight |
|---|---|---|
| A | Guar C261 N | 0.3 |
| | Water (overall) to | 100 |
| B | SBB | 35.0 |
| C | preservative (as required) | ca 1 |
| | Arlatone 1489 | 2.0 |
| D | Perfume (Blue Water ex Dragocco) | 0.3 | was made up by heating the water to about 80° C., dispersing the modified guar in the water under gentle stirring, adding the SBB under gentle stirring and maintaining the temperature at about 75 to 80° C. until the mixture was homogeneously dispersed, adding the preservative and Arlatone 1489 under gentle stirring and then cooling to ambient temperature under gentle stirring and adding the perfume when the temperature is about 35° C. The final product has a viscosity after one month of about 47 Pa.s (spindle E). This laboratory scale preparation was repeated in a 100 kg scale pilot plant run with similar successful results.

FE23—2 in 1 Scrub formulation—A formulation having the composition:

| | Material | parts by weight |
|---|---|---|
| A | Keltnol F | 0.2 |
| | Water (overall) to | 100 |

-continued

| Material | | parts by weight |
|---|---|---|
| B | SBB | 30.0 |
| C | preservative (as required) | ca 1 |
| D | Florabeads | 5.0 | was made up by heating the water to about 80° C., dispersing the xanthan in the water under gentle stirring, adding the SBB under gentle stirring and maintaining the temperature at about 75 to 80° C. until the mixture was homogeneously dispersed, adding the preservative and then cooling to ambient temperature under gentle stirring and adding the scrub agent under gentle stirring at about 35° C. The final product has a viscosity after one month of about 36 Pa.s (spindle E).

FE24—2 in 1 wash formulation with vegetable oil—A formulation having the composition:

| Material | | parts by weight |
|---|---|---|
| A | Keltnol F | 0.2 |
| | Water (overall) to | 100 |
| B | SBB | 31.0 |
| C | preservative (as required) | ca 1 |
| | glycerine | 2.0 |
| D | Florasun 90 | 2.0 |
| | Perfume (Blue Water) | 0.3 | was made up by heating the water to about 80° C., dispersing the xanthan in the water under gentle stirring, adding the SBB under gentle stirring and maintaining the temperature at about 75 to 80° C. until the mixture was homogeneously dispersed, adding the preservative and glycerine under gentle stirring and then cooling to ambient temperature under gentle stirring and adding the perfume and Florasun oil under gentle stirring at about 35° C. The final product has a viscosity after one month of about 28 Pa.s (spindle E). This laboratory scale preparation was repeated in a 5 kg scale pilot plant run with similar successful results.

FORMULATION EXAMPLE 25 (a and b)

This Example illustrates the inclusion of modified starches in formulated products. Formulations were made up having the following composition

| Material | | parts by weight |
|---|---|---|
| A | Modified Starch | 2.0 |
| | SBB | 30.0 |
| | Water (overall) to | 100 |
| B | preservative (as required) | ca 1 | by heating the water to about 80° C., dispersing the modified starch in the water under gentle stirring, adding the SBB under gentle stirring and maintaining the temperature at about 75 to 80° C. until the mixture was homogeneously dispersed, adding the preservative under gentle stirring and then cooling to ambient temperature under gentle stirring. For these laboratory tests, emollient and perfume were not added but can be added to make a commercial product as described above. The particular materials used and results of viscosity and stability testing are given in Table 2 below (columns labelled "sp" indicate which viscometer spindle was used).

FORMULATION EXAMPLE 26 (a to c)

This Example illustrates the use of modified starches in formulated products. Formulations were made up having the following composition

| Material | parts by weight |
|---|---|
| SBC | 30.0 |
| preservative (as required) | ca 1 |
| Water (overall) to | 100 | by heating the water to about 80° C., dispersing the SBC in the water under gentle stirring at about 75 to 80° C. until the mixture was homogeneously dispersed, adding the preservative under gentle stirring and then cooling to ambient temperature under gentle stirring. One sample was made up omitting starch from the surfactant blend (adjusting amounts in the final formulation to compensate). For these laboratory tests, emollient and perfume were not added but can be added to make a commercial product as described above. The particular materials used and results of viscosity and stability testing are given in Table 2 below.

FORMULATION EXAMPLE 27

Formulations FE 27 was made up as described in FE26 except that the hydrocolloid used in the SBC was a combination of 1.7 parts by weight of Clearam CH 40 and 3.3 parts by weight of wheat starch. The materials used and testing results are included in Table 2 below.

FORMULATION EXAMPLE 28 (a to c)

These Formulations were made up as described in FE26 generally using wheat starch as the hydrocolloid with the following exceptions:

FE 28a replacing the sodium cocoyl isethionate by an equal amount of sulphosuccinate surfactant (the formulation used 12.5 parts by weight of Tensiomild HM 935).

FE 28b the amount of structurant wax was increased to 2.4 parts by weight and the tallow alcohol was reduced to 2.4 parts by weight.

FE 28c the amount of tallow alcohol used was 4.8 parts by weight without any structurant wax.

The product of FE28b had a very good feel despite relatively high viscosity. Quantitative testing results for these Formulations are included in Table 3 below.

FORMULATION EXAMPLE 29

A surfactant blend with the following composition was made up:

| Material | parts by weight |
|---|---|
| sodium cocoyl isethionate | 4 |
| sodium lauryl sulphosuccinate | 6 |
| betaine surfactant | 0.3 |
| tallow alcohol | 3.6 |
| structurant wax | 0.6 |
| wheat starch | 4 |
| humectant etc. | 2 |

A dispersed formulated product was made up from this surfactant blend as described in FE26. The dispersion was very liquid and on preparation had a relatively low viscosity. The dispersion became somewhat more viscous after storage for 1 week.

FORMULATION EXAMPLE 30

Formulation FE 30 was made up as described in FE26 except that the structurant wax used in the SBC in was replaced with an equal weight of glyceryl mono-stearate. The dispersion was very liquid having a relatively low viscosity.

FORMULATION EXAMPLE 31 (a and b)

Surfactant blends with the following composition were made up:

| Material | parts by weight | |
|---|---|---|
| | FE31a | FE31b |
| sodium cocoyl isethionate | 4 | 4 |
| sodium lauryl sulphosuccinate | 6 | 6 |
| betaine surfactant | 0.3 | 0.3 |
| tallow alcohol | 3.6 | 3.6 |

-continued

| Material | parts by weight | |
|---|---|---|
| | FE31a | FE31b |
| structurant wax | 0.6 | 0.6 |
| wheat starch | — | 5 |
| Guar C261 N | 0.3 | 0.3 |
| humectant etc. | 2 | 2 |

Formulated dispersions in water FE31a and FE31b were made as described in FE26 (reducing the amount of FE31a to compensate for the absence of wheat starch). It appeared that the Guar contributed to the body of both formulations. The product without wheat starch was the more fluid at 40° C., but was still viscous at 50° C. Both formulations had very good skin feel.

TABLE 1

| FE No | Emolient/Oil Material | OV | IT | % SBA | Viscosity (Pa · s) 1 day | 1 month | Storage stability (1 month) 5° C. | Amb | 40° C. | 50° C. |
|---|---|---|---|---|---|---|---|---|---|---|
| 8a | Arlamol HD | 38.6 | 3.0 | 25 | 2.4 | 18.0 | +++ | +++ | +++ | +++ |
| 8b | | | | 33 | 20.0 | 48.0 | +++ | +++ | +++ | +++ |
| 8c | | | | 38 | 80.0 | 80.0 | +++ | +++ | +++ | +++ |
| 9a | Arlamol POAB | 80.5 | 28.5 | 25 | 1.9 | 20.0 | +++ | +++ | ++(S) | +++ |
| 9b | | | | 33 | 21.0 | 32.0 | +++ | +++ | ++(S) | +++ |
| 9c | | | | 38 | 55.0 | 59.0 | +++ | +++ | ++(S) | +++ |
| 10a | Sunflower Oil | 70.5 | 23.9 | 25 | 1.9 | 19.0 | +++ | +++ | +++ | +++ |
| 10b | | | | 33 | 36.0 | 67.0 | +++ | +++ | +++ | +++ |
| 10c | | | | 38 | 80.0 | 133.0 | +++ | +++ | +++ | +++ |
| 11a | Arlamol M 812 | 20.2 | 20.2 | 25 | 2.6 | 21.0 | +++ | +++ | +++ | +++ |
| 11b | | | | 33 | 64.0 | 86.0 | +++ | +++ | +++ | +++ |
| 11c | | | | 38 | 86.0 | 119.0 | +++ | +++ | +++ | +++ |
| 12a | Arlamol DOA | 7.5 | 27.0 | 25 | 2.4 | 23.0 | +++ | +++ | +++ | +++ |
| 12b | | | | 33 | 50.0 | 66.0 | +++ | +++ | +++ | +++ |
| 12c | | | | 38 | 62.0 | 86.0 | +++ | +++ | +++ | +++ |
| 13a | Arlamol E | 74.0 | 5.2 | 25 | 26.0 | 30.0 | +++ | +++ | +++ | +++ |
| 13b | | | | 33 | 55.0 | 44.0 | +++ | +++ | +++ | +++ |
| 13c | | | | 38 | 108.0 | 70.0 | +++ | +++ | +++ | +++ |
| 14a | Silicone Oil | 350.0 | 12.7 | 25 | 1.9 | 25.0 | +++ | +++ | +++ | +++ |
| 14b | | | | 33 | 27.0 | 44.0 | +++ | +++ | +++ | +++ |
| 14c | | | | 38 | 39.0 | 78.0 | +++ | +++ | +++ | +++ |
| 15a | Glycerine | 610.0 | — | 25 | 2.4 | 21.0 | +++ | +++ | +++ | +++ |
| 15b | | | | 33 | 21.0 | 41.0 | +++ | +++ | +++ | +++ |
| 15c | | | | 38 | 37.0 | 92.0 | +++ | +++ | +++ | +++ |

TABLE 2

| FE No | Modified Starch | Viscosity (Pa · s) 1 day | sp | 1 month | sp | Storage stability (1 month) 5° C. | Amb | 40° C. | 50° C. |
|---|---|---|---|---|---|---|---|---|---|
| 25a | Clearam CH 40 | 41.3 | E | 53.0 | F | +++ | +++ | +++ | +++ |
| 25b | Glycidex V17 | 40.6 | E | 45.2 | E | +++ | +++ | +++ | +++ |
| 26a | no starch | 1.2 | A | 14.8 | E | +++ | +++ | ++(S) | +++ |
| 26b | wheat starch | 0.8 | B | 46.8 | E | +++ | +++ | ++(S) | +++ |
| 26c | Clearam CH 40 | 10.1 | E | 126.4 | F | +++ | +++ | +++ | +++ |
| 27a | Clearam CH 40 + wheat starch | 13.1 | B | 49.9 | E | +++ | +++ | ++(S) | +++ |

TABLE 3

| FE | | Viscosity (Pa · s) | | | | Storage stability (1 month) | | | |
|---|---|---|---|---|---|---|---|---|---|
| No | Composition notes | 1 day | sp | 1 month | sp | 5° C. | Amb | 40° C. | 50° C. |
| 28a | sulphosuccinate but no SCl | 87.3 | F | >300 | F | +++ | +++ | +++ | +++ |
| 28b | increased structurant wax | 0.2 | A | 50.7 | E | +++ | +++ | ++(S) | +++ |
| 28c | no structurant wax | 0.2 | A | 31.2 | E | +++ | +++ | 0 | 0 |

Key to Stability test data in Tables 1 to 3
+++ Composition stable
++ minor separation—(S) indicates slight synerisis
+ significant separation—(S) indicates significant synerisis
o the composition has substantially all separated.

What is claimed is:

1. A method of making a stable aqueous foaming surfactant dispersion, comprising dispersing in water, at a temperature of from 60 to 90° C., a preformed, substantially uniform, solid surfactant composition comprising at least one foaming surfactant and at least one fatty amphiphile, in weight proportions to give a dispersion containing from 5 to 50 weight % of the surfactant composition and from 50 to 95 weight % water, homogeneously dispersing the preformed, substantially uniform, solid surfactant composition and subsequently adding an emollient to the dispersion.

2. A method as claimed in claim 1 in which the pre-formed solid surfactant composition additionally comprises at least one hydrocolloid.

3. A method as claimed in claim 1 in which the surfactant is one or more of alkyl sulphates, alkyl sulphonates, alkyl ether sulphates, alkyl glycerol ether sulphonates, alkyl phosphate esters, ethoxylated alkyl phosphate esters, sarcosinates, taurate derivatives, alkyl sulphoacetates, hydroxyalkyl sulphonate esters, alkyl sulphosuccinates, alkyl sulphosuccinamates, and acyl glutamates.

4. A method as claimed in claim 1 in which the fatty amphiphile is one or more of fatty alcohols, fatty acids, glyceride fatty esters, and esters of fatty acids with polyhydric alcohols.

5. A method as claimed in claim 2 in which the hydrocolloid is one or more of starch, modified starches or dextrins, guar, modified guar, modified celluloses, xanthan gums, hydrophilic carbomer polymers polyacrylamides, polyvinyl alcohol, polyvinylpyrrolidone, polyacrylates, very high molecular weight polyethylene glycol, water dispersible bentonite clays and aluminium silicates.

6. A method as claimed in claim 1 in which the emollient is at least one or more normally liquid emollient oils, emollients which are solid at room temperature or mixtures thereof, wherein said normally liquid emollient oils are selected from mineral or paraffin oils, vegetable glyceride oils, animal glyceride oils, synthetic ester oils, silicone oils, and said emollients which are solid at room temperature are selected from jojoba wax, tallow wax, coconut wax, tallow oil, coconut oil, and mixtures thereof.

7. A method as claimed in claim 1 in which the foaming surfactant comprises at least 50% by weight of at least one mild surfactant.

8. A method as claimed in claim 7 in which the mild surfactant is an alkyl sulphonate and/or a fatty isethionate.

* * * * *